(12) United States Patent
Jurrissen et al.

(10) Patent No.: US 10,241,184 B2
(45) Date of Patent: Mar. 26, 2019

(54) EPI GHOST CORRECTION INVOLVING SENSE

(71) Applicant: KONINKLIJKE PHILIPS N.V., Eindhoven (NL)

(72) Inventors: Michel Paul Jurriaan Jurrissen, Eindhoven (NL); Johannes Petrus Groen, Eindhoven (NL); Miha Fuderer, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 227 days.

(21) Appl. No.: 15/128,131

(22) PCT Filed: Mar. 20, 2015

(86) PCT No.: PCT/EP2015/055862
§ 371 (c)(1),
(2) Date: Sep. 22, 2016

(87) PCT Pub. No.: WO2015/144569
PCT Pub. Date: Oct. 1, 2015

(65) Prior Publication Data
US 2017/0108571 A1 Apr. 20, 2017

(30) Foreign Application Priority Data
Mar. 28, 2014 (EP) .................................... 14162169

(51) Int. Cl.
*G01R 1/00* (2006.01)
*G01R 33/565* (2006.01)
(Continued)

(52) U.S. Cl.
CPC ... *G01R 33/56554* (2013.01); *G01R 33/4818* (2013.01); *G01R 33/5611* (2013.01);
(Continued)

(58) Field of Classification Search
CPC ........ G01R 1/00; A61K 6/00; A61K 2121/00; A61B 1/00; A61B 2217/00
See application file for complete search history.

(56) References Cited

U.S. PATENT DOCUMENTS

| | | | |
|---|---|---|---|
| 7,358,728 B2 * | 4/2008 | Nozaki | G01R 33/56563 324/307 |
| 8,072,215 B2 | 12/2011 | Fuderer | |

(Continued)

FOREIGN PATENT DOCUMENTS

| | | |
|---|---|---|
| WO | 2008004192 A2 | 1/2008 |
| WO | 2012047771 A2 | 4/2012 |

OTHER PUBLICATIONS

Buonocore et al "Image Based Ghost Correction for Interleaved EPI" Magnetic Resonance in Medicine 45, p. 96-108 (2001).

(Continued)

*Primary Examiner* — Jermele M Hollington
*Assistant Examiner* — Temilade Rhodes-Vivour (57) ABSTRACT

In an EPI acquisition sequence for magnetic resonance signals k-space is scanned along sets of lines in k-space along opposite propagation directions, e.g. odd and even lines in k-space. Phase errors that occur due to the opposite propagation directions are corrected for in a SENSE-type parallel imaging reconstruction. The phase error distribution in image space may be initially estimated, calculated form the phase difference between images reconstructed from magnetic resonance signals acquired from the respective sets of k-space lines, or from an earlier dynamic.

5 Claims, 3 Drawing Sheets

(51) Int. Cl.
   *G01R 33/561* (2006.01)
   *G01R 33/48* (2006.01)
   *G01R 33/58* (2006.01)
   *A61K 6/00* (2006.01)

(52) U.S. Cl.
   CPC ... *G01R 33/5616* (2013.01); *G01R 33/56545* (2013.01); *G01R 33/583* (2013.01); *A61B 2217/00* (2013.01); *A61K 6/00* (2013.01); *G01R 1/00* (2013.01)

(56) References Cited

U.S. PATENT DOCUMENTS

| | | | | |
|---|---|---|---|---|
| 2005/0033154 | A1* | 2/2005 | deCharms | G01R 33/4806 600/410 |
| 2009/0018433 | A1* | 1/2009 | Kassai | A61B 5/055 600/413 |
| 2013/0049756 | A1* | 2/2013 | Ernst | H05K 999/99 324/322 |
| 2014/0056496 | A1* | 2/2014 | Kwak | A61B 5/0263 382/131 |

OTHER PUBLICATIONS

Reeder et al "Referenceless Interleaved Echo-Planar Imaging" Magnetic Resonance in Medicine 41, p. 87-94 (1994).

Yang et al "Double Sampled Echo-Planar Imaging at 3 Tesla" Journal of Magnetic Resonance, vol. 113, p. 145-150 (1996).

Jeong et al "High Resolution Human Diffusion Tensor Imaging Using 2-D Navigated Multishot Sense EPI at 7T" Magnetic Resonance in Medicine vol. 69, p. 793-802 (2013).

Foxall et al "Rapid Iterative Reconstruction for Echo Planar Imaging" Magnetic Resonance in Medicine vol. 42, p. 541-547 (1999).

Kim et al Automatic Correction of Ehco Planar Imaging (EPI) Ghost Artifacts in Real Time Interactive Cardiac MRI Using Sensitivity Encoding, Journal of Magnetic Resonance Imaging, vol. 27, p. 239-245 (2008).

Winkelmann et al "Ghost Artifact Removal Using a Parallel Imaging Approach" Magnetic Resonance in Medicine, vol. 54, p. 1002-1009 (2005).

Kellman et al "Phased Array Ghost Elimination" NMR in Biomedicine, Vo. 19, p. 352-361 (2006).

Chen et al "Removal of EPI Nyquist Ghost Artifacts With Two Dimensional Phase Correction" Magnetic Resonance in Medicine, vol. 51, p. 1247-1253 (2004).

Yun et alGhost Artifact Reduction in EPI With Sensitivity Encoding (Sense), Proc. Intl. Soc. Mag. Reson. Med. vol. 13, p. 2179 (2005).

* cited by examiner

EPI GHOST CORRECTION INVOLVING SENSE

CROSS REFERENCE TO RELATED APPLICATIONS

This application is a U.S. national phase application of International Application No. PCT/EP2015/055862, filed on Mar. 20, 2015, which claims the benefit of EP Application Serial No. 14162169.8 filed on Mar. 28, 2014 and is incorporated herein by reference.

FIELD OF THE INVENTION

The invention pertains to a magnetic resonance imaging method which comprises an echo-planar imaging (EPI) acquisition sequence.

BACKGROUND OF THE INVENTION

An EPI acquisition of magnetic resonance signals is known from the paper 'Image-based ghost correction for interleaved EPI' in MRM 45(2001)96-108 by M. H. Buoncore and D. C. Zhu.

The known magnetic resonance imaging method addresses the problem that phase distortions in EPI sequences cause ghosts as a general function of the read-directions (x) and the phase encoding direction (y). Images are reconstructed using only the left-to-right or right-to-left k-space lines (with missing lines replaced with zeros). The optimal phase distortion at each (x,y) location is found from an iterative solution.

Further, the international application WO2012/047771 discloses a magnetic resonance imaging method in which aliased images are formed from data acquired in multiple EPI shots.

SUMMARY OF THE INVENTION

An object of the invention is to provide magnetic resonance imaging method with an EPI acquisition with a correction for ghosting that requires a less cumbersome computation.

This object is achieved by the magnetic resonance imaging method of the invention which comprises an echo-planar imaging (EPI) acquisition sequence which includes sampling of k-space for magnetic resonance signals to collect
  a ltr-data set ($m_{ltr}$) reconstructed from lines in k-space scanned along a positive traversal direction in k-space and
  a rtl-data set ($m_{rtl}$) reconstructed from lines in k-space scanned along a negative traversal direction in k-space,
the magnetic resonance signals of the ltr-data set and the rtl-data set being acquired with several RF receiver antennae having spatial sensitivity profiles
accessing a spatial phase error distribution for the ltr-data set and for the rtl-data set
forming a ltr-encoding matrix ($S_{ltr}$) from (i) the phase encoding of the lines in k-space scanned along a positive traversal direction in k-space, (ii) the spatial phase error distribution for the ltr-data set, and (iii) the spatial coil sensitivity profiles,
forming a rtl-encoding matrix from ($S_{rtl}$) (i) the phase encoding of the lines in k-space scanned along a negative traversal direction in k-space, (ii) the spatial phase error distribution for the rtl-data set, and (iii) the spatial coil sensitivity profiles,
combining the ltr-encoding matrix and the rtl-encoding matrix into a global encoding matrix S,
reconstructing a diagnostic magnetic resonance image (p) by resolving the encoding relationship between the ltr and rtl-data sets for the pixel-values ($p_j(r)$) of the magnetic resonance image:

$$Sp = \begin{bmatrix} S_{ltr} \\ S_{rtl} \end{bmatrix} p = \begin{pmatrix} m_{ltr} \\ m_{rtl} \end{pmatrix}.$$

An insight of the invention is that owing to phase errors, the encoding matrices for magnetic resonance images reconstructed from respectively the ltr-data set and rtl-dataset that are measured (sampled) from k-space lines traversed along a positive and negative propagation direction along the read-direction in k-space are different. Moreover, the phase errors are dependent on both the position along the read-out direction (x) and the phase encoding direction (y). The magnetic resonance signals are acquired by multiple receiver antennae (coils or coil-elements) having a spatial sensitivity profile. Accordingly, there is an encoding relationship established, similar as in the SENSE parallel imaging approach, between the ltr-data set and the final magnetic resonance image as well as between the rtl-data set and the diagnostic magnetic resonance image. This encoding relationship combines the gradient (phase) encoding, the phase errors that add to the phase encoding and the spatial sensitivity profiles that govern the linear combinations of pixel-values due to the undersampling in k-space that causes folding in image space. From both the rtl-data set and the ltr-dataset separate magnetic resonance images can be reconstructed and unfolding in the event undersampling occurs, is done on the basis of the spatial sensitivity profiles. This provides sufficient redundancy to solve the phase error distribution. The phase error distribution may be initially estimated, measured in a calibration stage, or obtained from a previous iteration or an earlier dynamic. On the basis of the spatial sensitivity profiles and the spatial phase error distribution a global encoding relationship is established between the juxtaposed ltr-dataset and rtl-dataset and the (pixel-values of) the final magnetic resonance image. A further insight of the present invention is that this global encoding relationship is generally redundant, depending on the sampling density in the phase-encoding direction. This redundancy allows a stable resolution the pixel-values ($p_j(r)$) of the magnetic resonance image from the encoding relationship to the ltr and rtl-data sets. This is done by generalised matrix inversion techniques to the juxtaposed global encoding matrix $$\begin{bmatrix} S_{ltr} \\ S_{rtl} \end{bmatrix}.$$

Alternatively, a least-squares minimization approach can be employed to obtain the final magnetic resonance image as the best fit to the encoding relationship. That is, a solution is sought of the global encoding relationship which has minimum least-squares deviation from an exact solution. Such techniques for resolution of these highly redundant encoding relationships between measured MR data and the pixels of the final magnetic resonance image are generally known per se from the field of SENSE-like parallel imaging techniques.

These and other aspects of the invention will be further elaborated with reference to the embodiments defined in the dependent Claims.

The different phase errors which occur in magnetic resonance signals acquired from k-space along positive and negative traversal directions, respectively can be derived as the subtraction phase image from the unfolded ltr-image and the unfolded rtl-image. The subtraction phase image forms the spatial phase error distribution. The unfolded ltr-image is derived from the ltr-data set and the unfolded rtl-image is derived from the rtl-data set. In practice these unfolded ltr-image and rtl-images are reconstructed from the odd and even lines in k-space of the EPI k-space trajectory. The reconstructed ltr-data set and rtl-data set may have a relatively low signal-to-noise ratio because of lower overdetermination or even underdetermination of their encoding relationships to the final reconstructed magnetic resonance image. This is caused by the relatively larger sampling separation in k-space of the sampled phase encoding lines. Because of the relatively low spatial frequency of the phase errors, the spatial phase error distribution can be accurately derived for the subtraction phase image, e.g. by filtering the subtraction phase image to even out variations caused by noise.

In a further implementation of the invention a more accurate subtraction phase image is obtained in an iterative manner. In a calibration stage, an initial spatial phase error distribution is measured. In a simple approach the calibration stage involves an EPI acquisition scanned along k-space lines in which each line is scanned along alternating propagation directions along the read-direction. The initial phase error distribution is then employed to correct for phase errors in the unfolded ltr-image and unfolded rtl-image. The resulting phase corrected unfolded ltr-image and phase corrected unfolded rtl-image are then used to derive a more accurate subtracted phase image which provides a spatial phase error distribution of the current iteration, which in turn can be employed in the next iteration to again correct for phase errors in the unfolded ltr-image and unfolded rtl-image. The spatial phase error distribution may be employed to further correct phase errors in the unfolded ltr-image and unfolded rtl-image in the next iteration. Instead of correcting for the phase errors in the ltr-image and the rtl-image; the phase correction may be directly applied to the diagnostic magnetic resonance image. In practice a few iterations are sufficient to achieve a sufficiently accurate correction for phase errors that are spatially distributed over both the read-direction and the phase encoding direction. In practice it often occurs that already an accurate phase error distribution is obtained after the first iteration. Thus, when a dynamic series of EPI acquisitions is made, then for each dynamic only one iteration is sufficient to achieve an accurate dynamic series of phase error distributions for individual dynamics of the series. Such a dynamic series is usually acquired in an functional MRI (fMRI) examination in which the temporal behaviour of BOLD-signals in the blood vessels in the patient's brain are studied.

In another implementation of the invention, in the calibration stage an EPI acquisition is done having one set of lines in k-space each scanned first along a positive and then along a negative propagation direction and having another set of lines in k-space each scanned first along a negative and then along a positive propagation direction. That is, in the calibration stage the k-space trajectories are similar to those that lead to the rtl-data set and the ltr-data sets. This approach corrects in part for signal modulations due to different acquisition time moments along the k-space lines traversed along positive and negative propagation directions in k-space. Notably, this approach equals the average acquisition times of the ltr-data set and the rtl-data set. The proposed calibration scan has a purpose to provide separate 2D phase maps for the two readout directions. For this purpose a smaller set of phase encodings is used and all lines are acquired for both readout directions. The extra traversal of the $k_y=0$ line is done to achieve equal average timing of both sets. This is avoids contamination of the phase difference by e.g., $B_0$-offset induced phase shifts. The two ltr signal of the $k_y=0$ line have to be combined in an appropriate way.

In another more refined implementation the line along zero-phase encoding is scanned in k-space first along a positive traversal, then along a negative traversal and finally again along a positive traversal. This enables having the average acquisition times of the ltr-data set and the rtl-data set in a single shot EPI acquisition.

In this invention in an EPI acquisition sequence for magnetic resonance signals k-space is scanned along sets of lines in k-space along opposite propagation directions, e.g., odd and even lines in k-space. Phase errors that occur due to the opposite propagation directions are corrected for in a SENSE-type parallel imaging reconstruction. The phase error distribution in image space may be initially estimated, calculated from the phase difference between images reconstructed from magnetic resonance signals acquired from the respective sets of k-space lines, or from an earlier dynamic.

The invention further pertains to a computer program including instructions to control a magnetic resonance examination system to carry-out the method of the invention. The computer program of the invention can be provided on a data carrier such as a CD-ROM disk or a USB memory stick, or the computer program of the invention can be downloaded from a data network such as the world-wide web. When installed in the computer included in a magnetic resonance imaging system the magnetic resonance imaging system is enabled to operate according to the invention and enable the EPI acquisition with a correction for ghosting.

These and other aspects of the invention will be elucidated with reference to the embodiments described hereinafter and with reference to the accompanying drawings.

DETAILED DESCRIPTION OF THE EMBODIMENTS

Figure 1:
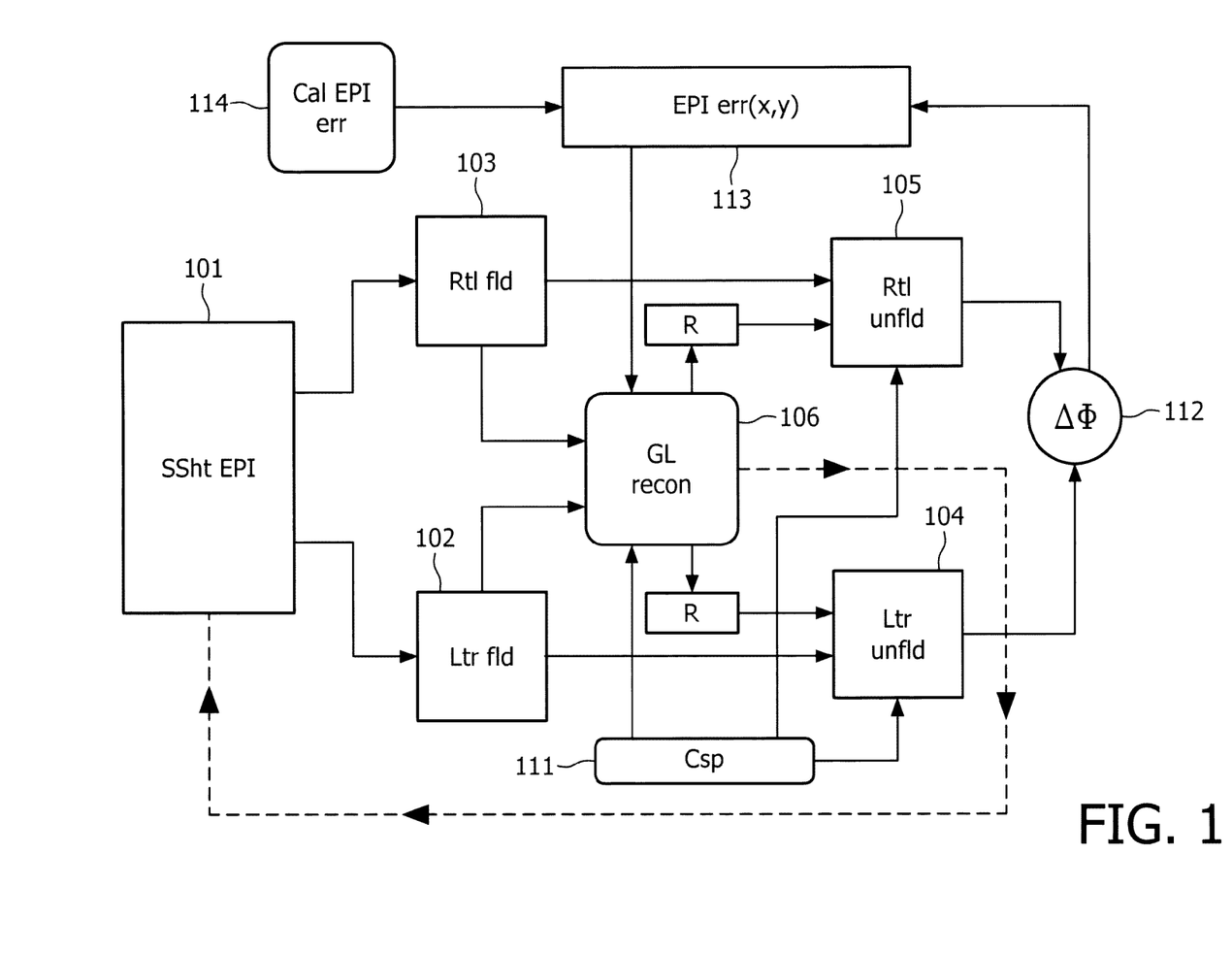
FIG. 1 shows a schematic representation of an implementation of the magnetic resonance imaging method of invention.
Figure 2:
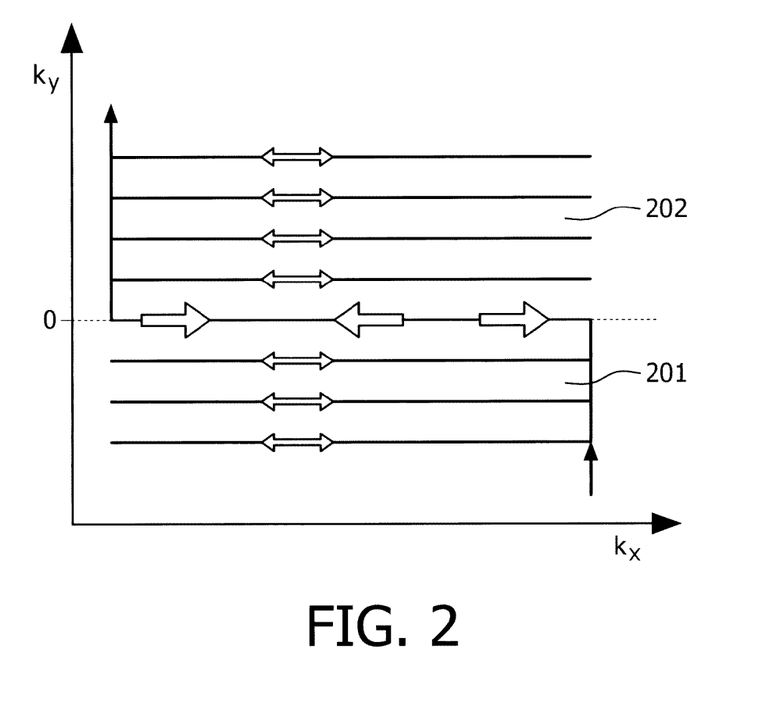
FIG. 2 shows a representation of an example of a two-dimensional k-space EPI trajectory for the calibration stage to measure the initial spatial phase error distribution is measured.

FIG. 1 shows a diagrammatic representation of an implementation of the magnetic resonance imaging method of the invention. In the single-shot EPI acquisition 101 two-dimensional k-space is scanned along lines in the positive propagation direction (left-to-right) and in the negative propagation direction (right-to-left). The data acquired in this manner form the ltr-data set and the rtl-data set. Typically, odd lines and even lines are scanned along opposite directions. From the data acquired by scanning along the positive propagation directions (e.g. the odd lines), that is from the ltr-data set the folded ltr-image 102 is reconstructed, typically by a fast-Fourier transformation of the ltr-data set. From the data acquired by scanning along the positive propagation directions (e.g. the odd lines), that is from the rtl-data set the folded rtl-image 103 is reconstructed, typically by a fast-Fourier transformation of the ltr-data set. Usually, the ltr-data (rtl-data) set formed by only the odd (even) lines will be under sampled in the phase-encoding direction in k-space giving rise to aliasing that manifests itself as folding artefacts. The folded ltr-image and the folded rtl-image are unfolded 104, 105 by way of a SENSE reconstruction that makes use of the coil sensitivity profiles 111. This SENSE reconstruction is known as such and usually employed for reconstruction of data that are undersampled in k-space in order to reduce the acquisition time of the data. From the unfolded ltr-image 104 and the unfolded rtl-image 105 the phase difference image 112 is derived. This phase difference image contains the phase differences of the ltr-data set relative the rtl-data set. These phase differences are built-up from differences between the phase encodings and differences between phase errors in the ltr-data set and the rtl-data set that are caused by effects such as gradient switching delays, and eddy currents. Since the phase-encodings in the ltr-data set and in the rtl-data set are applied in a controlled manner, the spatial phase error distribution 113 can be derived from the phase difference image 112. To initialize the process, in the calibration stage 114 a first measurement of the spatial phase error distribution is measured by scanning two-dimensional k-space along a set of phase-encoding lines, where each line is scanned along opposite directions. The difference between the phase of the magnetic resonance signals acquired at opposite propagation directions represents the phase errors. Because the measurement is done at different phase-encoding values, the phase errors are measured in dependence of both the read-direction and the frequency encoding direction. This measured phase error distribution forms an initial estimate of the spatial phase error distribution. The phase error distribution may be obtained in various manners from the phase difference image, the measurement from the calibration stage and or the spatial phase error distribution 113 available from a previous iteration or from a previous dynamic. The phase error distribution could be simply replaced by the currently available phase difference image, but the current phase difference image may also be combined with the result from the calibration stage, from a previous dynamic or information retained. In this way account can be taken of a possibly higher noise level in the phase difference images as well as the result from the calibration stage becoming relatively outdated.

The diagnostic magnetic resonance image is reconstructed 106 on the basis of the spatial sensitivity profiles, the spatial phase error distribution and the global encoding relationship is established between the juxtaposed ltr-dataset and rtl-dataset and the (pixel-values of) the final magnetic resonance image. The pixel-values of the diagnostic magnetic resonance image can be employed for a regularisation approach in the unfolding (104, 105) of the rtl-folded image and the ltr-folded images. This regularisation improves the numerical stability of the unfolding of the rtl-folded image and the ltr-folded image and reduces the noise level in the unfolded images. Hence, the noise level in the phase-error distribution is reduced.

In the iterative approach, the diagnostic magnetic resonance image can be updated from time to time in successive iterations. Thus, at the current iteration, the regularisation can be done on relatively accurate pixel-values of the currently available version of the diagnostic magnetic resonance image which can be refreshed from time to time so as to account for the phase error distribution growing more accurate as the iterations progress.

Alternatively, in a dynamic approach (shown schematically by the dashed lines) successive single-shot EPI acquisitions are made. Thus, k-space acquisitions are done at successive instants in time, which then represent dynamic change that may occur in the object, such as due to movement caused by the patient's heartbeat and respiration. In such a dynamic approach, as an estimate of the phase error distribution, the result for the phase error distribution from an earlier, preferably the previous, dynamic may be employed. It appears that the phase error distribution only slowly varies over dynamics and it has also appeared in the iterative approach that often a single iteration is sufficient for an accurate determination of the phase error distribution.

In more mathematical detail, the reconstruction of the diagnostic magnetic resonance image from the single-shot EPI acquisition(s) is as follows. For the odd and even echoes (i.e. the ltr-dataset and the rtl-dataset) SENSE equations can be written as:

$$S\Phi_{even}\vec{p}=\vec{m}_{even}\ S\Phi_{odd}\vec{p}=\vec{m}_{odd}$$

S is the coil sensitivity matrix, m is the measured data and p the final image pixels of the unfolded ltr-image 104 and the unfolded rtl-image 105.

$\Phi$ is a diagonal matrix containing the delta phase encoding $\Delta\Phi_{enc}$ and the 2D EPI phase errors $\Phi_{epi}$:

$$\Phi = \begin{pmatrix} e^{(\varphi_{enc}(r_1)+\varphi_{epi}(r_1))} & 0 & 0 \\ 0 & \ddots & 0 \\ 0 & 0 & e^{(\varphi_{enc}(r_N)+\varphi_{epi}(r_N))} \end{pmatrix}$$

With N=2*R, where R is the SENSE reduction factor, and 2 the extra 'SENSE factor' by splitting the odd and even echoes. The sensitivity encoding, remaining phase encoding and phase errors can be combined in one 'sensitivity' matrix $S_{even}$ and $S_{odd}$.

$$S\Phi_{even}=S_{even}\ S\Phi_{odd}=S_{odd}$$

Let the even echoes contain the k=0 profile (so no delta phase encoding) and only a delta 2D EPI phase correction is applied to the odd echoes, now $\Phi$ for the even and odd echoes is:

$$\Phi_{even}=I,\ \Phi_{odd}=\begin{pmatrix} e^{(\Delta\varphi_{enc}(r_1)+\Delta\varphi_{epi}(r_1))} & 0 & 0 \\ 0 & \ddots & 0 \\ 0 & 0 & e^{(\Delta\varphi_{enc}(r_N)+\Delta\varphi_{epi}(r_N))} \end{pmatrix}$$

with $\Delta\Phi_{enc}(r) = iR\frac{2\pi}{FOV}r_{enc\_dir}$

This $\Delta\Phi_{enc}$ is purposely introduced to have a better separation between the sets of equations; it is created by the k-space-distance between the odd and even k-space lines. The SENSE equation can now be written as:

$$S_{even}\vec{p} = S\vec{p} = \vec{m}_{even}$$

$$S_{odd}\vec{p} = S'\vec{p} = \vec{m}_{odd} \ (S_{odd} = S')$$

Combining the odd and even echoes in one so-called SENSE-IRIS reconstruction kernel:

$$\begin{bmatrix} S \\ S' \end{bmatrix} \vec{p} = \begin{bmatrix} \vec{m}_{even} \\ \vec{m}_{odd} \end{bmatrix} \rightarrow S_{all}\vec{p}_{all} = \vec{m}_{all}$$

Where $p_{all}$ is the diagnostic magnetic resonance image resulting from odd-even echoes combined unfolding reconstruction including 2D EPI phase correction.

Now to determine the EPI phase changes over dynamics, the odd and even echoes can additionally be reconstructed separately. For example for the even echoes holds $$S\vec{p} = \vec{m}_{even} + \vec{n}_n \ N_n = N(0, \Psi_n)$$

$$\vec{p} = \vec{p}_{all} + \vec{n}_p \ N_p = N(0, f(\vec{p}_{all})) = N(0, R)$$

Here $p_{all}$ is used to regularize (R) the reconstruction. Function f needs to be tuned and 'instructs' the SENSE reconstruction how close the solution is to the previous full solution ($p_{all}$). The noise contribution is $n_n$ to the measured data. The reconstruction of the unfolded pixels may include reconstruction uncertainties and errors which is accounted for by the term $n_p$. In a regularisation approach in the unfolding it is assumed that the unfolding solution is close to the reference $p_{all}$. This reference can be obtained from a previous solution such as (1) the solution of the previous iteration or (2) the solution of the previous dynamic.

Regularisation matrix R typically depends on the modulus of $p_{all}$:

$$R^{-1/2} = F \cdot \begin{bmatrix} |\vec{p}_{all,r_1}| & 0 \\ 0 & |\vec{p}_{all,r_{Sf}}| \end{bmatrix}$$

The size of the matrix is equivalent to the number of SENSE folded pixels (Sf). If the solution is expected to differ 10% from $p_{all}$, F=0.1. If the previous dynamic is used for regularisation, and the expected changes (by heating) are small (e.g. 1%), F can be chosen smaller (e.g. 0.01). In an iterative reconstruction f can be reduced (stronger regularisation) for the higher iterations.

The SENSE solution for the even and odd echoes is:

$$\vec{p}_{even} = (S^H \Psi_n^{-1} S + R^{-1})^{-1} [S^H \Psi_n^{-1} R^{-1}] \begin{bmatrix} \vec{m}_{even} \\ \vec{p}_{all} \end{bmatrix}$$

$$\vec{p}_{odd} = (S'^H \Psi_n^{-1} S' + R^{-1})^{-1} [S'^H \Psi_n^{-1} R^{-1}] \begin{bmatrix} \vec{m}_{odd} \\ \vec{p}_{all} \end{bmatrix}$$

The phase difference image is now calculated by a simple subtraction:

$$\Delta\Phi_{EPI} = \text{angle}(\vec{p}_{even}) - \text{angle}(\vec{p}_{odd})$$

The separate SENSE reconstructions of the odd and even echoes result in lower SNR, due to higher SENSE geometry factors. So these images are not optimal for clinical use. But sufficient to determine a global 2D EPI phase change. For example fit $\Delta\Phi_{EPI}$ to a 2D linear phase error or strongly smooth the $\Delta\Phi_{EPI}$ map.

The estimated $\Delta\Phi EPI$ is added to the 2D EPI phase errors and used in the SENSE-IRIS reconstruction of the next dynamic, resulting in a dynamically updated 2D EPI phase correction, integrated in the SENSE reconstruction.

Figure 3:
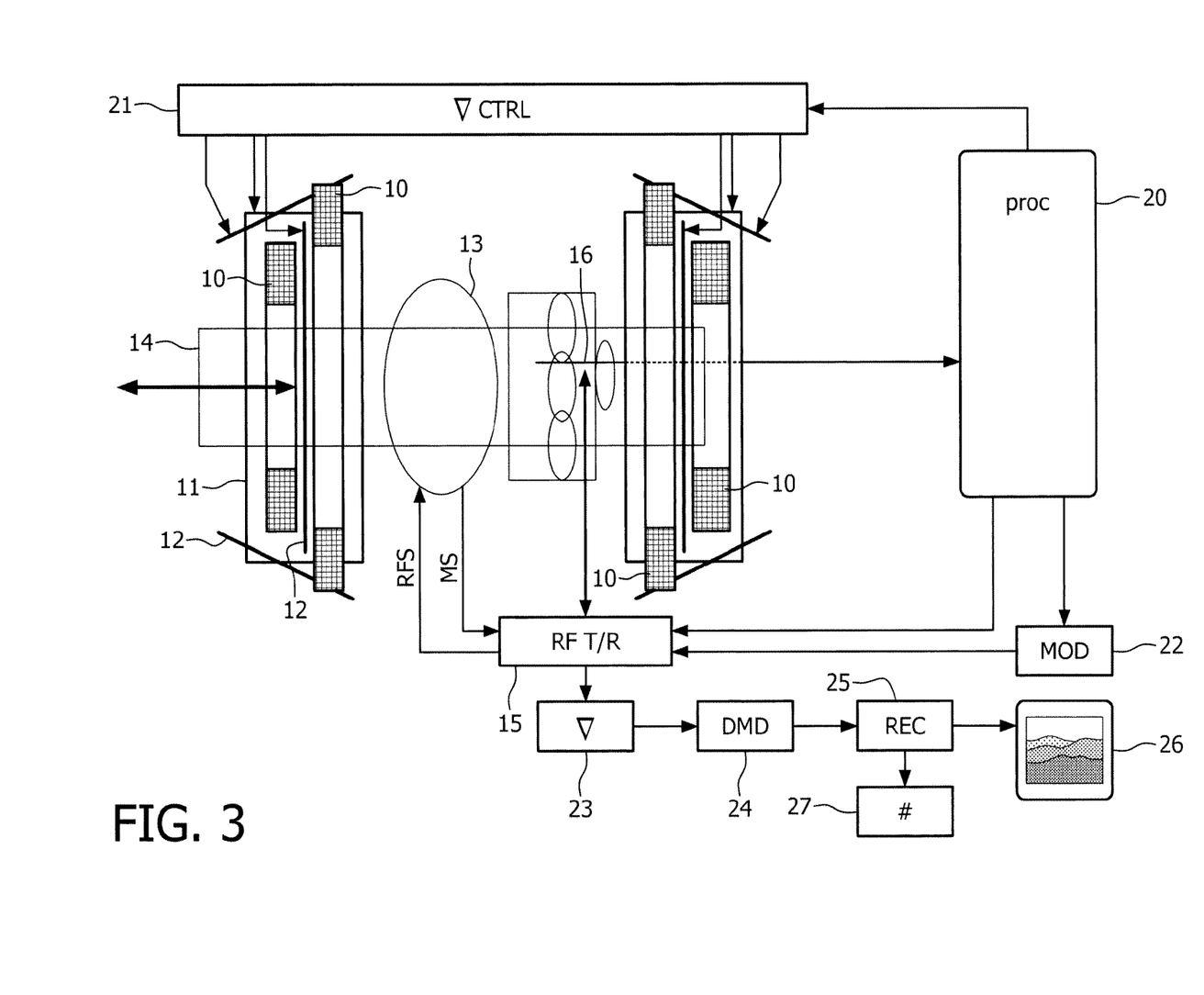
FIG. 3 shows a diagrammatic representation of a magnetic resonance examination system in which the present invention is incorporated.

The FIG. 3 shows diagrammatically a magnetic resonance imaging system in which the invention is used. The magnetic resonance imaging system includes a set of main coils 10 whereby the steady, uniform magnetic field is generated. The main coils are constructed, for example in such a manner that they enclose a tunnel-shaped examination space. The patient to be examined is placed on a patient carrier which is slid into this tunnel-shaped examination space. The magnetic resonance imaging system also includes a number of gradient coils 11, 12 whereby magnetic fields exhibiting spatial variations, notably in the form of temporary gradients in individual directions, are generated so as to be superposed on the uniform magnetic field. The gradient coils 11, 12 are connected to a controllable power supply unit 21, the gradient coils 11, 12 are energised by application of an electric current by means of the power supply unit 21; to this end the power supply unit is fitted with electronic gradient amplification circuit that applies the electric current to the gradient coils so as to generate gradient pulses (also termed 'gradient waveforms') of appropriate temporal shape. The strength, direction and duration of the gradients are controlled by control of the power supply unit. The magnetic resonance imaging system also includes transmission and receiving coils 13, 16 for generating the RF excitation pulses and for picking up the magnetic resonance signals, respectively. The transmission coil 13 is preferably constructed as a body coil 13 whereby (a part of) the object to be examined can be enclosed. The body coil is usually arranged in the magnetic resonance imaging system in such a manner that the patient 30 to be examined is enclosed by the body coil 13 when he or she is arranged in the magnetic resonance imaging system. The body coil 13 acts as a transmission antenna for the transmission of the RF excitation pulses and RF refocusing pulses. Preferably, the body coil 13 involves a spatially uniform intensity distribution of the transmitted RF pulses (RFS). The same coil or antenna is usually used alternately as the transmission coil and the receiving coil. Furthermore, the transmission and receiving coil is usually shaped as a coil, but other geometries where the transmission and receiving coil acts as a transmission and receiving antenna for RF electromagnetic signals are also feasible. The transmission and receiving coil 13 is connected to an electronic transmission and receiving circuit 15.

It is to be noted that it is alternatively possible to use separate receiving and/or transmission coils 16. For example, surface coils 16 can be used as receiving and/or transmission coils. Such surface coils have a high sensitivity in a comparatively small volume. The receiving coils, such as the surface coils, are connected to a demodulator 24 and the received magnetic resonance signals (MS) are demodulated by means of the demodulator 24. The demodulated magnetic resonance signals (DMS) are applied to a reconstruction unit. The receiving coil is connected to a preamplifier 23. The preamplifier 23 amplifies the RF resonance signal (MS) received by the receiving coil 16 and the amplified RF resonance signal is applied to a demodulator 24. The demodulator 24 demodulates the amplified RF resonance signal. The demodulated resonance signal contains the actual information concerning the local spin densities in the part of the object to be imaged. Furthermore, the transmission and receiving circuit 15 is connected to a modulator 22. The modulator 22 and the transmission and receiving circuit 15 activate the transmission coil 13 so as to transmit the RF excitation and refocusing pulses. The reconstruction unit derives one or more image signals from the demodulated magnetic resonance signals (DMS), which image signals represent the image information of the imaged part of the object to be examined. The reconstruction unit 25 in practice is constructed preferably as a digital image processing unit 25 which is programmed so as to derive from the demodulated magnetic resonance signals the image signals which represent the image information of the part of the object to be imaged. The signal on the output of the digital image processing unit 25 is provided to the reconstruction monitor 26, so that the monitor can display the magnetic resonance image. It is alternatively possible to store the signal from the reconstruction unit 25 in a buffer unit 27 while awaiting further processing.

The magnetic resonance imaging system according to the invention is also provided with a control unit 20, for example in the form of a computer which includes a (micro) processor. The control unit 20 controls the execution of the RF excitations and the application of the temporary gradient fields. To this end, the computer program according to the invention is loaded, for example, into the control unit 20 and the reconstruction unit 25.

The invention claimed is:

1. A magnetic resonance imaging method, comprising;
employing an echo-planar imaging (EPI) acquisition sequence which includes sampling of k-space for magnetic resonance signals to collect;
an ltr-data set ($m_{ltr}$) reconstructed from lines in k-space scanned along a positive traversal direction in k-space, and
an rtl-data set ($m_{rtl}$) reconstructed from lines in k-space scanned along a negative traversal direction in k-space,
the magnetic resonance signals of the ltr-data set and the rtl-data set being acquired with several RF receiver antennae having spatial sensitivity profiles, the method further comprising;
accessing a spatial phase error distribution for the ltr-data set and for the rtl-data set,
forming an ltr-encoding matrix ($S_{ltr}$) from (i) a phase encoding of the lines in k-space scanned along the positive traversal direction in k-space, (ii) a spatial phase error distribution for the ltr-data set, and (iii) spatial coil sensitivity profiles,
forming an rtl-encoding matrix from ($S_{rtl}$) (i) a phase encoding of the lines in k-space scanned along the negative traversal direction in k-space, (ii) a spatial phase error distribution for the rtl-data set, and (iii) the spatial coil sensitivity profiles,
combining the ltr-encoding matrix and the rtl-encoding matrix into a global encoding matrix S, and
reconstructing a diagnostic magnetic resonance image (p) by resolving an encoding relationship between the ltr-data set and the rtl-data set for the pixel values ($p_j(r)$) of the magnetic resonance image:

$$Sp = \begin{bmatrix} S_{ltr} \\ S_{rtl} \end{bmatrix} p = \begin{pmatrix} m_{ltr} \\ m_{rtl} \end{pmatrix},$$

wherein:
at least one of the ltr-data set and the rtl-data set is undersampled in k-space,
an unfolded ltr-image is derived from the ltr-data set as a solution of an encoding relationship between the ltr-data set and pixel values of the unfolded ltr-image:

$$S_{ltr}p_{ltr}=m_{ltr},$$

an unfolded rtl-image is derived from the rtl-data set as a solution of the encoding relationship between the rtl-data set and pixel values of the unfolded rtl-image:

$$S_{rtl}p_{rtl}=m_{rtl},$$

a subtraction phase image is formed from the unfolded ltr-image and the unfolded rtl-image, and the subtraction phase image is employed as the spatial phase error distribution,
an initial spatial phase error distribution is measured in a calibration stage,
a phase corrected unfolded ltr-image is formed in that the unfolded ltr-image or the ltr-data set is corrected by the initial spatial phase error distribution,
a phase corrected unfolded rtl-image is formed in that the unfolded ltr-image or the rtl-data set is corrected by the initial spatial phase error distribution,
the subtraction phase image is formed from the phase corrected unfolded ltr-image and the phase corrected unfolded rtl-image, and
the phase corrected unfolded ltr-image and the phase corrected unfolded rtl-image are generated in an iterative manner.

2. The magnetic resonance imaging method of claim 1, in which the phase corrected unfolded ltr-image and phase corrected unfolded rtl-image are employed to derive a more accurate subtracted phase image which provides a spatial phase error distribution of a current iteration, which, in turn is employed in a next iteration to again correct for phase errors in the unfolded ltr-image and unfolded rtl-image.

3. The magnetic resonance imaging method as claimed in claim 1 wherein the initial spatial phase error distribution is measured in the calibration stage in which an EPI acquisition is done having one set of lines in k-space each scanned first along a positive propagation direction and then along a negative propagation direction, and having another set of lines in k-space each scanned first along the negative propagation direction and then along the positive propagation direction.

4. The magnetic resonance imaging method of claim 3 in which a line along zero-phase encoding is scanned in k-space first along a positive traversal, then along a negative traversal and finally again along a positive traversal.

5. A computer program for controlling a magnetic resonance examination system and comprising instructions stored on a non-transitory computer readable medium, which when executed causes the magnetic resonance examination system to:
apply an echo-planar imaging (EPI) acquisition sequence which includes sampling of k-space for magnetic resonance signals to collect:

an ltr-data set ($m_{ltr}$) reconstructed from lines in k-space scanned along a positive traversal direction in k-space, and an rtl-data set ($m_{rtl}$) reconstructed from lines in k-space scanned along a negative traversal direction in k-space, acquire magnetic resonance signals of the ltr-data set and the rtl-data set with several RF receiver antennae having spatial sensitivity profiles, access spatial phase error distributions for the ltr-data set and for the rtl-data set, form an ltr-encoding matrix ($S_{ltr}$) from a phase encoding of the lines in k-space scanned along the positive traversal direction in k-space, (ii) a spatial phase error distribution for the ltr-data set, and (iii) the spatial sensitivity profiles, form an rtl-encoding matrix from ($S_{rtl}$) (i) a phase encoding of the lines in k-space scanned along the negative traversal direction in k-space, (ii) a spatial phase error distribution for the rtl-data set, and (iii) the spatial sensitivity profiles, combine the ltr-encoding matrix and the rtl-encoding matrix into a global encoding matrix S, reconstruct a magnetic resonance image (p) by resolving an encoding relationship between the ltr-data set and the rtl-data set and pixel values ($p_j(r)$) of the magnetic resonance image:

$$\begin{bmatrix} S_{ltr} \\ S_{rtl} \end{bmatrix} p = \begin{pmatrix} m_{ltr} \\ m_{rtl} \end{pmatrix},$$

undersample at least one of the ltr-data set and the rtl-data set in k-space, derive an unfolded ltr-image from the ltr-data set as a solution of an encoding relationship between the ltr-data set and pixel values of the unfolded ltr-image:

$$S_{ltr} p_{ltr} = m_{ltr},$$

derive an unfolded rtl-image from the rtl-data set as a solution of an encoding relationship between the rtl-data set and pixel values of the unfolded rtl-image:

$$S_{rtl} p_{rtl} = m_{rtl},$$

form a subtraction phase image from the unfolded ltr-image and the unfolded rtl-image, and employ the subtraction phase image as the spatial phase error distribution for the ltr-data set, measure an initial spatial phase error distribution in a calibration stage, form a phase corrected unfolded ltr-image in that the unfolded ltr-image or the ltr-data set is corrected by the initial spatial phase error distribution, form a phase corrected unfolded rtl-image in that the unfolded ltr-image or the ltr-data set is corrected by the initial spatial phase error distribution, and form the subtraction phase image from the phase corrected unfolded ltr-image and the phase corrected unfolded rtl-image and in which the phase corrected ltr-image and the phase corrected rtl-image are generated in an iterative manner.

\* \* \* \* \*